United States Patent [19]

Clagett et al.

[11] 4,127,124

[45] Nov. 28, 1978

[54] URETHANE BIOIMPLANT MEMBRANE

[75] Inventors: Donald C. Clagett, Lincoln; Michael J. Svetly, Medford; Peter H. Scott, Sudbury, all of Mass.

[73] Assignee: W. R. Grace & Co., Cambridge, Mass.

[21] Appl. No.: 796,218

[22] Filed: May 12, 1977

[51] Int. Cl.$^2$ .................. C08J 9/00; A61L 15/00; C08G 18/06; C08G 18/08
[52] U.S. Cl. .................................... 128/156; 128/296; 3/1; 428/315; 428/320; 428/322; 521/63; 521/159; 521/905
[58] Field of Search ........ 260/2.5 A, 2.5 BB, 2.5 AN, 260/2.5 AP, 2.5 AY, 2.5 AD, 77.5 AM, 77.5 AA, 75 TN; 428/315, 320, 322; 128/156; 3/1

[56] References Cited

U.S. PATENT DOCUMENTS

| | | | |
|---|---|---|---|
| 3,812,619 | 5/1974 | Wood et al. | 260/2.5 |
| 3,823,111 | 7/1974 | Loew et al. | 260/2.5 AY |
| 3,895,134 | 7/1975 | Kigane et al. | 260/2.5 AY |
| 3,903,232 | 9/1975 | Wood et al. | 260/2.5 AD |
| 3,905,923 | 9/1975 | Klug | 260/2.5 AD |
| 3,978,266 | 8/1976 | Lock | 260/2.5 AD |
| 3,978,855 | 9/1976 | McRae et al. | 128/156 |

*Primary Examiner*—V. P. Hoke
*Attorney, Agent, or Firm*—Lowell H. McCarter; C. Edward Parker; Edward J. Hanson, Jr.

[57] ABSTRACT

Bioimplant three dimensional latice of hydrophilic polyurethane having a backbone of polyetherol or polyesterol, end-capped with aliphatic or aromatic diisocyanate, chain branched with polyol and bound into a latice by chain extension alkyl diols. The method of producing such a latice. An extension would be the use of the latice for other medical and veterinary purposes.

32 Claims, No Drawings

URETHANE BIOIMPLANT MEMBRANE

BACKGROUND OF THE INVENTION

The present invention is specifically concerned with bioimplants for mammals. More broadly the invention has application to any situation when a material is needed for contact with living mammalian tissue wherein a substantially non-irritating or minimal biological response is needed.

In general every foreign material placed in the body causes at least some slight degree of response which may be thought of largely as the body's defense against invasion by foreign substances.

Polyurethane surgical dressings have been proposed in the past as represented by U.S. Pat. Nos. 3,978,266 and 3,978,855. Patent 3,978,855 mentions at the top of Col. 2 that polyurethane foam cell structures cause inflammatory cells to be attracted when impressed into the dermis or when the polyurethane material breaks away and comes to lie in the developing connective tissue under the epidermis.

SUMMARY OF THE INVENTION

A method is provided for producing a substantially unfoamed microporous hydrophilic bioimplant membrane. The method involves reacting a first component comprising isocyanate end-capped polyol chosen from the group consisting of polyetherol, polyesterol and mixtures thereof and having a reaction functionality of at least two with a second component comprising a diol in an isocyanate monomer to diol molar ratio of 1 to 3.5. The reaction is carried out in a solvent reaction medium at a total solids concentration of less than 25% and the solvent is volatilized at a rate not causing the reaction product to foam. The membrane is implanted within the living tissue of a mammal.

By preferred aspects of the invention the isocyanate capped polyetherol or polyesterol is a diisocyanate end-capped polyetherol and is dissolved in a solvent reaction medium to form a stock solution and the diol is $C_2$ to $C_6$ diol and dissolved in a solvent reaction medium to form an activator solution and the reaction is brought about by combining the stock solution and the activator solution. In a preferred form a mono-alcohol is included in the solvent reaction medium as a reactant. The hydrophilic member is preferably free of silicon agents and chlorofluorocarbons and has levels of free diisocyanate not exceeding 0.005 millimoles/gram and levels of free amines not exceeding 210 parts per million.

By another aspect the general method is followed to provide a biononirritating material, not an unfoamed microporous bioimplant membrane. By nonirritating it is meant relatively benignant as will be further understood hereinafter.

By another aspect of the invention a bioimplant member is provided comprising a microporous molecular lattice of hydrophilic polyurethane. The polyurethane has a backbone chosen from the group consisting of polyetherols and polyesterols, or mixture thereof and is end-capped with isocyanate chosen from the group consisting of aliphatic isocyanates and aromatic isocyanates. The urethane has chain branching centers of polyol and the branched urethane chains are bound by diol chain extension to form continuous three dimensional lattices.

In preferred aspects the diisocyanate end-capped polyetherol or polyesterol is an etherol having an average molecular weight of less than 1250, the diol is a $C_2$ to $C_5$ diol, and the molar ratio of isocyanate monomer to diol is 1 to 3.5. In yet another aspect mono-alcohol is included as chain stops for some of the urethane chains. In other preferred aspects the member is free of silicon agents and chlorofluorocarbons and has levels of free diisocyanate not exceeding .005 millimoles/gram and levels of free amines not exceeding 210 parts per million and said member is implanted within living mammalian tissue.

By lattice it is not meant to imply a geometrically regular structure but only a random structure.

DESCRIPTION OF THE PREFERRED EMBODIMENT

The present invention, in a preferred embodiment is a bioimplant membrane implanted within the living tissue of a mammal. The membrane is a microporous hydrophilic polyurethane prepared by reacting an aliphatic or aromatic diisocyanate end-capped polyetherol or polyesterol with a diol chain extender. By end-capped it is meant a diisocyanate reacted as an adduct to the hydroxyl functionality of a polymer or branching polyol via urethane linkage to produce isocyanate terminated polymers as described in "Polyurethane Technology", P. F. Bruins (Editor), Interscience Publishers, New York, in particular pages 9–11. In some cases the polyurethane is alcohol chain stopped.

The aliphatic and/or aromatic diisocyanate end-capped polyetherol prepolymers employed in the present invention may broadly be compounds of this class such as are described in U.S. Pat. No. 3,812,619 and British Pat. No. 1,429,711 the subject matter of which are incorporated by reference into this application. Diisocyanate end-capped polyesterol prepolymers may be aliphatic or aromatic (or combinations thereof). An example of an appropriate polyesterol would be an aliphatic-aromatic combination such as the condensation polymer of terphthalic acid and ethylene glycol. Such compounds are available from a variety of commercial sources. The prepolymer materials to be useful in the present invention have a reaction functionality of at least two.

The preferred prepolymers are those produced from polyetherol or polyesterols diols of 500–1500 g/mole molecular weight, however under the proper circumstances the following additional polyols will be of particular use: polyethylene glycols of 1500–4000 g/mole and polyesterols from 500–4000g/mole. Preferably the prepolymers are those produced using aliphatic end-caps such as isophorone diisocyanate and hexamethylene diisocyanate. However under the proper circumstances, aromatic diisocyanates such as toluene diisocyanate, benzene diisocyanate and 4,4'-diphenylmethylene diisocyanate may be used to advantage. The preferred molar ratio of diisocyanate to polyol in the prepolymer is 3.32 to 8.80. In general the reaction functionality greater than two is achieved by blending a polyhydroxyorganic of hydroxy functionality greater than two such as the most preferred trimethylolpropane with the polyetherol or polyesterol in molar ratio of 0.5 to 2.0.

The activator, curing agent or chain extender is a diol. The preferred diols are the $C_2$ to $C_6$ alkyl diols or polyetherol oligomers. The most preferred activator is butane-1, 4-diol, however under the proper circumstances the preferred activators are ethyleneglycol, propane-1, 2-diol, propane-1, 3-diol, butane-1,2-diol, pentane-1, 2-diol, pentane-1, 3-diol, pentane-1, 5-diol, hexane-1, 2-diol, and hexane-1, 6-diol and the like may be used. Other preferred diols include polyoxyethylene oligomers including diethylene glycol, trimethylene glycol and the like.

The prepolymer and activator by an aspect of this invention are reacted in a reaction medium. The medium should be inert to the reactants and therefore anhydrous to prevent foaming and precuring. The reaction medium should be readily removable from the reaction product, preferrably by vaporization, to provide microporosity. The removal of the reaction medium should be very thorough to reduce the number of materials to which the living tissue is exposed and may include flushing of the membrane with water or water solutions prior to implantation.

Preferably the reaction medium will also serve as a carrier for the prepolymer and the activator to simplify their combination. Thus the preferred reaction medium is a solvent for both the prepolymer and the activator and they in turn are soluble in the reaction medium. The preferred solvent for the prepolymer or stock solution and the activator solution is anhydrous acetone however under the proper circumstances such as requirements for altering rates of vaporization, other anhydrous solvents or mixtures thereof may be used to advantage, for example, acetone, methylethylketone, and diethylketone or combination thereof and the like. Other solvents can be used such as toluene, benzene, and combination of these solvents or the previously cited ketones and other possible 5 or 6 carbon ketones.

The preferred molar ratio of the isocyanate monomer in the prepolymer to diol compound of the activator is 1 to 3.5, more preferably 1.5 to 3 and most preferably about 2 or more specifically 2.25 as illustrated by Example 1.

The total solids concentration should be less than 25% based on 100% of the total reaction composition including the solids. The preferred solids concentration is 0.5 to 10% and the more preferred concentration is 0.5 to 2%. Most preferably about 1% solids solutions are used. The higher total solids solutions are necessary when mechanical requirements of the coated implant are such as to require thicker membranes.

It is an aspect of the invention that a prepolymer stock solution be prepared. The stock solution would be comprised of the prepolymer and a portion of the reaction medium. This stock solution can be stored for a short period of time, up to a month or more, without substantial gelation caused by precuring. This allows for shipment and the like and easy combining in the reaction medium.

The activator may within the purview of this aspect of the invention also be prepared by solution in the reaction medium. The activator solution has an indefinite storage-shipping life. It only needs to be protected against loss by volatilization of the components. Of course both the stock solution and the activator solutions need to be sealed against water contamination from such sources as the moisture in ambient air.

A mono-alcohol may also be advantageously included in the reaction mixture. This is advantageously done by adding the mono-alcohol to the activator solution. This may be done without deleteriously effecting the storage stable qualities of the activator solution. The mono-alcohol acts as a chain stopper in the reaction products polymerization.

The preferred mono-alcohol is ethyl alcohol but under the proper circumstances other mono-alcohols may be used such as, and in particular, methanol, 1-propanol, 2-propanol, 1-butanol, 2-butanol, or 1-pentanol and the like.

While the prepolymer preparation is not itself a part of this invention certain aspects of its preparation are of significance because the prepolymer yield with its residual contents effects the reaction product bioimplant membrane of the present invention. For example, the preferred isocyanate end-capped polyoxyethylene polyols are those in which either stannous octoate or dibutyltin were the catalysts of preparation. Further the preferred antioxidants present in the prepolymer are 2,6-disubstituted hindered phenols such as 2,2'-methylene-bis (4-methyl-6-(2-methyl cyclohexyl) phenol).

The resulting membrane is a polyetherol or polyesterol backbone branched via triol or polyolcenters through polyurethane functionality linked end-caps, which in turn are bound via alkyl diol polyurethane linked extentions to form a continuous three dimensional latice. When the chain stopping alcohols are used the continuous three dimensional latice will be interruped randomly by alkoxyurethane terminated side chains. The operable and preferred characteristics of the components of the latice have already been described and will not be repeated here.

The membranes can be used to encase materials such as metals that would stimulate the body to build fibrous materials and produce other defenses to invasion by materials sensed by the body as foreign. Yet the membrane is porous so contact can be maintained between the body and the material encased. The membrane can also be used to dispense medicines and in this instance may be particularly useful in domestic animals.

While the present invention is concerned with bioimplant membranes, the prior art mentioned at the beginning of this application suggest that the compositions of the present invention could be used for other medical and veterinary purposes. For example, the compositions could be foamed by addition of water, water and amine, or water and alcohol and used as surgical dressings. Other example uses would be burn dressings and artificial skin.

The compositions are of particular advantage as bioimplantable membranes because they are relatively free of chlorofluorocarbons and silicon agents and have a low level of free diisocyanate and a low level of free amines derived from the diisocyanate. By low level of free diisocyanate it is meant that the millimoles/gram of free isocyanate in the finished polymer will be less than .005. By low level of free amine it is meant that the amine will be less than 210 parts/million. That this is a significantly low diisocyanate and amine content is known as may be seen for example in the "Journal of Cellular Plastics" July–August, 1976, pages 222–226.

The procedure for determining free diaminoorganics down to the 20 parts per million level is ±30% and is performed using fluorometric procedures. The method for amino residues in bioimplant membranes involves extracting with methanol, separation by thin layer chromatography and fluorometric assay with Fluram® reagent obtainable from Roche Diagnostics Division of Hoffman-LaRoche, Inc.

The procedure for free isocyanate in urethanes is performed using the Kubitz quantitative test "Analytical Chemistry", Vol. 29, pages 814–816 (1957). The presence of isocyanate at levels at or above 210 parts per million causes the Kubitz reagent, which is a complex of n-butylamine and malacite green, to turn green.

EXAMPLES

In the following examples pledgets of aliphatic or aromatic diisocyanate end-capped polyetherol or polyesterol, diol chain extended, and in some cases alcohol chain stopped hydrophilic biocompatable polyurethanes were prepared and implanted in guinea pigs.

EXAMPLE 1

A polyurethane stock solution was prepared by charging 1.37 grams of the isocyanate capped polyetherol given for Example 1 in Table 1 and 147.64 grams of dry acetone into an 8 ounce size tin plated paint can under a dry nitrogen atmosphere at ambient temperature of about 25° C. A dry friction top was secured on the can and the can was thoroughly shaken by hand to mix the contents. The diisocyanate end-capped polyetherol was prepared from the materials given for Example 1 in Table 1 in the following manner. The isocyanate is added in two stages. In the first stage about 95% of the amount theoretically necessary to cap all the hydroxyl groups in the polyol is added followed by the second addition of about 15% of the theoretical amount necessary to cap all of the hydroxyl groups to provide a total of 110% of the theoretical amount. Between the incremental additions to the reaction mixture the mixture is heated at about 50°–80° C. for approximately 2 hours.

An activator solution was prepared by charging 8.77 grams of dry acetone, 1.23 grams of anhydrous, 1, 4-butanediol and 0.126 grams of absolute ethanol into a glass vial under atmospheric conditions and ambient temperature. The vial was vapor sealed with a polyethylene stopper and shaken by hand to mix the contents.

The stock solution and the activator solution were then shipped to another location which consumed several days in transit. The stock solution is storage stable up to a month or more and the activator solution is storage stable substantially indefinitely. The stock solution and 1 gram of the activator solution were combined and thoroughly mixed to form a membrane forming solution under anhydrous conditions. The stock solution was then placed in a friction top tin plated paint can until used.

Eighteen pledgets of the membrane formed from the membrane forming solution were then prepared. The pledgets were prepared by coating eighteen individual waffers by submerging the waffers in the membrane forming solution, removing the coated waffers from the solution and curing the membrane coating at about 70° C. until solvent evolution was completed.

The pledgets were submitted for biocompatability studies. Two pledgets were implanted beneath the panniculus carnosus over the lateral abdomen in 9 guinea pigs. Three guinea pigs bearing the pledgets were sacrificed 4 days, 12 days and 21 days after implantation of the pledgets. Paraffin sections were then prepared of each pledget. The pledgets elicited two distinct reactions, (1) an immediate cellular infiltrate of varying type and degree derived from blood borne elements and (2) an activation of preexisting fibroblasts to varying degrees. Either reaction if severe enough would preclude use of the polyurethane inside the body. However, these reactions will occur to some extent during implantation of any material in either a guinea pig's or human's body. The results of the biocompatability study are given in Table 2.

EXAMPLES 2–8

The procedures and formulations of Examples 2–8 were the same as described for Example 1 except as indicated in Table 1 and the notations following. The results of the biocompatability studies are given in Table 2 together with the results of corresponding biocompatability studies done on control membrane materials.

TABLE 1

BIOIMPLANTABLE MEMBRANE FORMULATIONS

| | STOCK SOLUTION | | | | | | ACTIVATOR SOLUTION | | | | |
|---|---|---|---|---|---|---|---|---|---|---|---|
| | Characteristics of isocyanate capped polyetherol | | | | | | | | | Reaction Mixture | |
| | Isocyanate Capped Polyetherol | Isocyanate capped polyetherol Molar Ratios of Components | | | | Catalyst*/ | Solvent | Diol | Alcohol | Solvent | Stock Sol. | Activator Solution |
| Ex. | (g) | Polyol | TMOP | TDI | IPDI | Antioxidant** | (g) | (g) | (g) | (g) | (g) | (g) |
| 1 | (1.37) | PEG-1000 (2.0) | (1.0) | | (7.70) | Yes/No | Acetone (147.6) | (1.10) | (0.13) | Acetone (8.78) | 149 | 1 |
| 2 | (1.37) | PEG-1000 (2.0) | (1.0) | | (7.70) | Yes/No | Acetone (147.6) | (1.23) | | Acetone (8.77) | 149 | 1 |
| 3 | (1.43) | PEG-1500 (2.0) | (1.0) | (6.65) | | No/No | Acetone (147.6) | (0.94) | | Acetone (9.26) | 149 | 1 |
| 4 | (1.37) | PEG 1000 (2.0) | (1.0) | (6.65) | | No/Yes | Acetone (147.6) | (1.06) | | Acetone (8.85) | 149 | 1 |
| 5 | (1.41) | PEG 1500 (2.0) | (1.0) | (7.70) | | No/No | Acetone (147.6) | (0.94) | | Acetone (9.07) | 149 | 1 |
| ***6 | (13.4) | PEG 1000 (2.0) | (1.0) | (7.70) | | No/Yes | Acetone (147.6) | (0.80) | (0.10) | Acetone (8.90) | 40 | 10 |
| 7 | (1.37) | PEG 1000 (2.0) | (1.0) | (6.65) | | No/Yes | Acetone (147.6) | (0.95) | (0.10) | Acetone (8.90) | 149 | 1 |
| 8 | 0412712401-303 (0.5) | PEG 4000 (1.0) | | (4.40) | | No/Yes | Acetone (147.6) | (0.68) | | Acetone (9.32) | 149 | 1 |

*0.02% stannous octoate
**0.02% various 2, 6 hindered phenols
***Higher percentage solids (10%) used in order to provide a heavy coating for implantation. The normal 1% solids was mechanically too friable for implantation
PEG-0000 - Polyethylene glycol, Average Molecular Wt.
TMOP - trimethylolpropane
TDI - Toluene diisocyanate
IPDI - Isophorone diisocyanate
(g) - grams

TABLE 2
GUINEA PIG HISTOLOGICAL FINDINGS

| | 4 DAYS | | | | | | 12 DAYS | | | | |
|---|---|---|---|---|---|---|---|---|---|---|---|
| Ex. | Round Cell | Fibroblast reaction | Neutrophil Cells | Edema | Mesenchymal React. | Misc. Thick. | Focal tion | Fibroblast Reac-Fibrosis | Cell | Round mal React. | Mesenchy-Misc. |
| 1 | Slight | Slight Activation | | | | Slight Mesothelial cell othelial | Few | Minimal | | | |
| 2 | " | " | | | | " | | " | | | |
| 3 | minimal | " | | | | | | | | | |
| 4 | " | 6–10 | None | | | Re-orient. Conn. tissue | | | 0.5mm tissue response | | Slight mesothelial reaction |
| 5 | " | cell layer | | | | | | | | Minimal | " |
| 6 | Slight | | | | Slight | | | | | Heavy | Moderate round cell reaction |
| 7 | Infiltra. | Early | | | | | Moderate | | | Gone | |
| 8 | " | | Infiltra. | Yes | | | | Fibrinoid necrosis | Present | Neutrophi | Edema and Present |
| Control* | | | | | | | | | | | |
| A | Slight Present | Very Slight | Slight | | | | Minimal | | | | No cell reaction |
| B | sent | | Few | Yes | Slight | | | Heavy | | | |
| C | Many | | | Yes | Very Active | | Dense | | | | |
| D | Present | | | Yes | Activation | | | Moderate | | | Tumor |
| E | Material too porous which induced excessive fibroblast reaction. | | | | | | | | | | |

| | 21 DAYS | | | | |
|---|---|---|---|---|---|
| Example | Fibroblast Reaction | Epithelical Effect | Fibrosis | Misc. | Implantation Utility in Guinea Pig Panniculus Carnosus |
| 1 | Minimal | | | | Good |
| 2 | " | | Slight | | Possible |
| 3 | | | Low | | Possible |
| 4 | | | 0.5mm tissue response | Few Red Cells | Reject** |
| 5 | | | Moderate | Plastic Degradation | Reject** |
| 6 | some Resorption | Yes | High | | Reject** |
| 7 | 1mm layer | | Excess | no Round cells | Reject** |
| 8 | | | Dense | Cellular Resp. Plastic Degrad. | Reject** |
| Control* | | | | | |
| A | Minimal | | | No Cell Reaction | Good |
| B | | | Moderate | | Reject |
| C | | | High | | Possible |
| D | | | Moderate | | Reject |
| E | | | | | Reject |

Control*
A Hydroxymethylmethacrylate (Biolon)
B Porous Polypropylene
C Silastic Silicon
D Silastic grade silicon rubber
E Polyurethane foam
**Although the plastics were not suitable for this application the degree of failure does not preclude their being considered for other implantation.

The histologic results in Table 2 show an increasing degree and extent of tissue trauma from the bioimplant membranes of Example 1 to those of Example 8. When compared to Table 1 these results suggest that the composition of Examples 1 and 2 are most preferable, that 3 and 4 are more preferable and that 5–8 are preferable to foamed polyurethanes (Control E) and as good as or better than other implantable membrane substances such as Controls A–D. The most preferable performance of the lower numbered examples we believe may be ascribed to their better tissue compatibility.

This compatibility is thought to be due to two main influences. Firstly, the hydrophilic nature of the membranes of this invention allows them to successfully interact through hydrogen and electrostatic bonds with bodily chemicals and fluids such as nucleic acids, proteins, carbohydrates, and aqueous fluids and serums. Secondly, the best bioimplant polyurethane membranes should be soft enough to preclude undue stiffness which results in physical irritation to bodily tissues or microfractures which can expose the coated implant to bodily tissues or present sharp edges for irritation of bodily tissues. Such softness can be analogized to flexibility which can theoretically be obtained by altering the potential flexibilities of the end capping agent. For example, isophorone diisocyanate has longer intra-isocyanate bond distances than either 2,6- or 2,4-toluene diisocyanate and thus would be expected to promote flexibility. An increase in the amount of end capping agent would be expected to decrease flexibility. However, it would be expected that reduction of end capping would at some point tend to degrade film properties. End capped short chain polymers would be expected to result in stiffer films than longer chain end capped polymers.

Examples 1 and 2 whose membrane contain the isophorone end-capped PEG 1000 polymers, therefore, are observed to be better implants than Examples 3,4,6 and 7 which are PEG 1000 polymers end-capped with toluene diisocyanate. Example 3 is a toluene diisocyanate end-capped polyetherol with improved flexibility due to its use of the longer chain PEG 1500 and, hence, is a better implant than examples 4,6 and 7. Examples 3 and 5 are similar but differ in that 3 has a higher level of toluene diisocyanate. Hence, Example 5 is stiffer and of poorer performance than Example 3. Example 8 apparently has a lower than sufficient level of diisocyanate to make a viable plastic membrane in this use. However, Examples 1–8 may all have utility for other medical or veterinary uses including implantation at other sites.

Subtle adjustments in membrane performance can be made by use of chain stopping alcohols. It is believed that such chain stopping results in random free alkoxyurethane terminated chains which give the surface of the membrane a higher surface area of a character enhancing the abilities of bodily tissues and fluids to effect necessary hydrogen and electrostatic bonds for relatively benign tissue and fluid recognition.

We claim:

1. A method of implanting an unfoamed microporous hydrophilic bioimplant membrane within the living tissue in a mammal comprising the steps of producing a substantially unfoamed microporous hydrophilic bioimplant membrane by reacting a first component comprising isocyanate end-capped polyol chosen from the group consisting of polyetherol, polyesterol and mixtures thereof and having a reaction functionality of at least two with a second component comprising a $C_2$ to $C_6$ diol in an isocyanate monomer to diol molar ratio of 1 to 3.5 in a non-aqueous solvent reaction medium at a total solids concentration of less than 25%, volatilizing the solvent at a rate not causing the reaction product to foam whereby said unfoamed microporous hydrophilic bioimplant membrane is produced and placing the membrane so produced within the living tissue of a mammal.

2. The method of claim 1 wherein the membrane is implanted beneath the panniculus carnosus.

3. A method of placing a hydrophilic biononirritating material within the living tissue in a mammal comprising producing a hydrophilic biononirritating material by reacting a first component comprising isocyanate end-capped polyol chosen from the group consisting of polyetherol, polyesterol and mixtures thereof and having a reaction functionality of at least two with a second component comprising a $C_2$ to $C_6$ diol in an isocyanate monomer to diol molar ratio of 1 to 3.5 in a non-aqueous solvent reaction medium at a total solids concentration of less than 25%, volatilizing the solvent whereby said hydrophilic biononirritating material is produced and placing the material within the living tissue of a mammal.

4. The method of claim 3 wherein the material is placed beneath the panniculus carnosus.

5. A method of producing a substantially unfoamed microporous hydrophilic bioimplant membrane comprising reacting a first component comprising isocyanate end-capped polyol chosen from the group consisting of polyetherol, polyesterol and mixtures thereof and having a reaction functionality of at least two with a second component comprising a $C_2$ to $C_6$ diol in an isocyanate monomer to diol molar ratio of 1 to 3.5 in a non-aqueous solvent reaction medium at a total solids concentration of less than 25% and volatilizing the solvent at a rate not causing the reaction product to foam and producing said unfoamed microporous hydrophilic bioimplant membrane.

6. The method of claim 1 wherein said isocyanate is an aliphatic diisocyanate; the diol is an alkyl diol, polyetherol oligomer or mixture of 2 or more of them; the solvent is a 3 to 5 membered ketone or mixture thereof; and the total solids concentration is 0.5 to 10%.

7. The method of claim 6 wherein said alphatic diisocyanate in the prepolymer is isophoronediisocyanate, the $C_2$ to $C_6$ diol is butane-1,4-diol, the solvent is acetone and the total solids concentration is 0.5 to 2%.

8. The method of claim 1 wherein a mono-alcohol chain stopper is included in the solvent reaction medium as a reactant.

9. The method of claim 1 wherein the isocyanate capped polyetherol or polyesterol is a diisocyanate end capped polyetherol and is dissolved in a non-aqueous solvent reaction medium to form a stock solution and said $C_2$ to $C_6$ diol is dissolved in a non-aqueous solvent reaction medium to form an activator solution and said reaction is brought about by combining said stock solution and said activator solution.

10. The method of claim 1 wherein said unfoamed microporous hydrophilic bioimplant membrane is free of silicon agents and chloroflurocarbons and has levels of free diisocyanate not exceeding 0.005 millimoles/gram and levels of free amines not exceeding 210 parts per million.

11. The method of claim 9 wherein said diisocyanate end-capped polyetherol has an average molecular weight of less than 1250, said diol is a $C_2$ to $C_5$ diol, the solvent is a 3 to 5 membered anhydrous ketone or mixture thereof, the total solids concentration is 0.5 to 10% and the molar ratio of isocyanate monomer to diol is 1.5 to 3.

12. The method of claim 11 wherein said diisocyanate end-capped polyetherol is polyoxyethylene polyol and said diisocyanate capped polyoxyethylene polyol was prepared with a stannous octoate catalyst and contains a 2,6-disubstituted hindered phenol as an antioxidant, said diol is butane-1,4-diol, said solvent is acetone, the total solids concentration is 0.5 to 2%, the molar ratio of isocyanate monomer to diol is about 2, and said unfoamed microporous hydrophilic membrane is free of silicon agents and chlorofluorocarbons and has levels of free diisocyanate not exceeding 0.005 millimoles/gram and levels of free amines not exceeding 210 parts per million.

13. A bioimplant member comprising a microporous molecular lattice of hydrophilic polyurethane, said polyurethane having a backbone chosen from the group consisting of polyetherols and polyesterols, or mixtures thereof, said backbone end-capped with isocyanate selected from the group consisting of aliphatic isocyanates and aromatic isocyanates, said urethane having chain branching centers of polyol, said branched urethane chains being bound by a $C_2$ to $C_6$ diol chain extension to form continuous three dimensional lattices and said urethane having a molar ratio of isocyanate to diol of from 1 to 3.5.

14. The member of claim 13 wherein some of the urethane chains are chain stopped with alcohol.

15. The member of claim 13 wherein said isocyanate is an aliphatic diisocyanate; the diol is a $C_2$ to $C_6$ alkyl diol, polyetherol oligomer or mixture of 2 or more of them; the solvent is a 3 to 5 membered ketone or mixture thereof; and the total solids concentration is 0.5 to 10%.

16. The member of claim 13 wherein the isocyanate capped polyetherol or polyesterol is a diisocyanate end-capped polyetherol and said diol is a $C_2$ to $C_6$ alkyl diol.

17. The member of claim 13 wherein said microporous molecular lattice of hydrophilic polyurethane is free of silicon agents and chlorofluorocarbons and has levels of free diisocyanate not exceeding 0.005 millimoles/gram and levels of free amines not exceeding 210 parts per million.

18. The member of claim 16 wherein said diisocyanate end-capped polyetherol or polyesterol is an etherol having an average molecular weight of less than 1250, said diol is a $C_2$ to $C_5$ diol, and the molar ratio of isocyanate monomer to diol is 1 to 3.5.

19. The member of claim 18 wherein a mono-alcohol chain stopper is included.

20. The member of claim 19 wherein said etherol of said diisocyanate end-capped polyetherol is polyoxyethylene polyol and said diisocyanate capped polyoxyethylene polyol was prepared with a stannous octoate catalyst and contains a 2,6-disubstituted hindered phenol as an antioxidant, said diol is butane-1,4-diol, the molar ratio of isocyanate monomer to diol is 1.5 to 3, and said member is free of silicon agents and chlorofluorocarbons and has levels of free diisocyanate not exceeding .005 millimoles/gram and levels of free amines not exceeding 210 parts per million.

21. A method of producing a hydrophilic biononirritating material comprising reacting a first component comprising isocyanate end-capped polyol chosen from the group consisting of polyetherol, polyesterol and mixtures thereof and having a reaction functionality of at least two with a second component comprising a $C_2$ to $C_6$ diol in an isocyanate monomer to diol molar ratio of 1 to 3.5 in a non-aqueous solvent reaction medium at a total solids concentration of less than 25% and volatilizing the solvent and producing said hydrophilic biononirritating material.

22. The method of claim 21 wherein said isocyanate is an aliphatic diisocyanate; the diol is an alkyl diol, polyetherol oligomer or mixture of 2 or more of them; the solvent is a 3 to 5 membered ketone or mixtures thereof; and the total solids concentration is 0.5 to 10%.

23. The method of claim 22 wherein said aliphatic diisocyanate is isophoronediisocyanate, the diol is butane-1, 4-diol, the solvent is acetone and the total solids concentration is 0.5 to 2%.

24. The method of claim 21 wherein a mono-alcohol chain stopper is included in the solvent reaction medium as a reactant.

25. The method of claim 21 wherein the isocyanate end-capped polyetherol or polyesterol is a diisocyanate end-capped polyetherol and is dissolved in a non-aqueous solvent reaction medium to form a stock solution and said $C_2$ to $C_6$ diol is dissolved in a non-aqueous solvent reaction medium to form an activator solution and said reaction is brought about by combining said stock solution and said activator solution.

26. The method of claim 21 wherein said hydrophilic biononirritating material is free of silicon agents and chlorofluorocarbons and has levels of free diisocyanate not exceeding 0.005 millimoles/gram and levels of free amines not exceeding 210 parts per million.

27. The method of claim 25 wherein said etherol of said diisocyanate end-capped polyetherol is polyoxyethylene polyol with an average molecular weight of less than 1250, and said diisocyanate end-capped polyoxyethylene polyol was prepared with a stannous octoate catalyst and contains a 2,6-disubstituted hindered phenol as an antioxidant, said diol is butane-1,4-diol, said solvent is acetone, the total solids concentration is 0.5 to 2%, the molar ratio of isocyanate monomer to diol is 1.5 to 3, and said hydrophilic biononirritating material is free of silicon agents and chlorofluorocarbons and has levels of free diisocyanate not exceeding .005 millimoles/gram and levels of free amines not exceeding 210 parts per million.

28. A substantially biononirritating material comprising a hydrophilic polyurethane, said polyurethane having a backbone chosen from the group consisting of polyetherols and polyesterols, or mixtures thereof, said backbone end-capped with isocyanate chosen from the group consisting of aliphatic isocyanates and aromatic isocyanates, said urethane having chain branching centers of polyol, said branched urethane chains being bound by a $C_2$ to $C_6$ diol chain extension to form continuous three dimensional lattices and said urethane having a molar ratio of isocyanate to diol of from 1 to 3.5.

29. The material of claim 28 wherein some of urethane chains are chain stopped with alcohol.

30. The material of claim 28 wherein said diisocyanate end-capped polyetherol or polyesterol is an etherol having an average molecular weight of less than 1250 and said diol is a $C_2$ to $C_6$ alkyl diol.

31. The material of claim 30 wherein a monoalcohol chain stopper is included in the solvent reaction medium as a reactant.

32. The material of claim 31 wherein said etherol of said diisocyanate end-capped polyetherol is polyoxyethylene polyol and said diisocyanate capped polyoxyethylene polyol was prepared with a stannous octoate catalyst and contains a 2,6-disubstituted hindered phenol as an antioxidant, said diol is butane-1,4-diol, the molar ratio of isocyanate monomer to diol is 1.5 to 3, and said material is free of silicon agents and chlorofluorocarbons and has levels of free diisocyanate not exceeding 0.005 millimoles/gram and levels of free amines not exceeding 210 parts per million.

* * * * *